US00PP10027P

United States Patent [19]

Cully

[11] Patent Number: Plant 10,027

[45] Date of Patent: Sep. 16, 1997

[54] SWEET GUM TREE NAMED WARD

[75] Inventor: Earl Cully, Jacksonville, Ill.

[73] Assignee: Heritage Trees, Inc., Jacksonville, Ill.

[21] Appl. No.: 608,013

[22] Filed: Mar. 4, 1996

[51] Int. Cl.[6] ..... A01H 5/00

[52] U.S. Cl. ..... Plt./51.1

[58] Field of Search ..... Plt./51.1

*Primary Examiner*—James R. Feyrer
*Assistant Examiner*—Melissa L. Kimball
*Attorney, Agent, or Firm*—Foley & Lardner

[57] ABSTRACT

A new and distinct sweet gum tree named 'Ward' characterized by its nearly seedless habit, producing a very light crop of gumballs only a small number of which remain by autumn; excellent growth habit; winter hardiness, withstanding temperatures as low as −28° F. without damage, and by its beautiful corky bark.

7 Drawing Sheets

The present invention comprises a new and distinct variety of sweet gum tree, botanically known as *Liquidambar styraciflua*, and referred to by the cultivar name 'Ward'.

The new cultivar is the result of a graft made by the inventor Earl Cully in 1965 from budwood of a sweet gum tree growing in a cultivated area in Morgan County, Ill. The budwood was grafted on a sweet gum stock of no particular distinction. The tree from which the budwood was taken was never commercialized or publicly distributed and no longer exists.

Subsequent growth of the grafted tree resulted in the expression of the unique characteristics thereof which in combination distinguish 'Ward' from other cultivars of the species. Subsequent asexual reproduction of the tree by chip budding, grafting, and tissue culture, carried out first by the inventor in Jacksonville, Ill., and performed later in Olympia, Wash., has established that the unique characteristics of the new tree are carried from generation to generation. Asexual propagation by tissue culture has proved to be very consistent and effective.

The following characteristics in combination distinguish 'Ward' from other trees of the species:

1. Compared to the species, this new cultivar produces a very light crop of gum balls. Most that are produced will abort in mid-June when they are still very small and soft. By autumn, only a small number remain on the tree. These few remaining balls do not become the typical hard, stonelike fruits with shapr pointed spines, but remain soft and underdeveloped.

2. The exaggerated and bizarre corky wings on the smaller branches. The wings are thin (approximately 2 mm at base) and vary in length (up to 7 cm or more) and height (to 1.5 cm). The wings may develop on second-year wood and are found on all branch planes and may even spiral around the branch. Wings that do not remain intact break up into dull, thorn-like pinnacles. This very unusual corky wing formation is a clearly unique feature of the new tree.

3. The new cultivar is more winter hardy than other trees of the species. It has withstood temperatures to −28°F. without noticeable damage, making it winter hardy in the lower half of USDA Zone 5A and all of Zone 5B.

4. The leaves of 'Ward' are somewhat larger than leaves of other trees of the species.

5. The new cultivar is a vigorous grower with a straight central leader. During its early years, growth habit is generally narrow pyramidal, with the tree later developing a medium oval crown. Summer foliage is a lustrous dark green, with fall color ranging from deep burgundy to red when the tree is grown in the open.

Reference is now made to the several colored photographs which collectively comprise the photographic drawings.

The photo on Sheet 1 is a winter view of the new cultivar.

The photo on Sheet 2 is an actual size view of a typical leaf from the new tree.

The photograph on Sheet 3 illustrates the unique exaggerated corky bark development on the branches.

The photograph on Sheet 4 illustrates bud development on a two-year grafted tree.

The photo on Sheet 5 is of a relatively young tissue cultured tree of the new cultivar which exhibits corky bark formation on three-month old branches.

The photo on Sheet 6 is of a two-year budded tree of the new cultivar, showing corky bark development on two-year branches.

The photo on Sheet 7 is closeup view of the tree illustrated in the photo on Sheet 6 and showing branches of a two-year budded tree with corky bark development. The extent of the development will be apparent from the photograph.

The new tree has not been observed under all possible environmental conditions. The phenotype may vary somewhat with variations and environments without, however, any variance in the genotype.

The following observations and measurements are taken from the mature tree illustrated in the photograph on Sheet 1 of the application drawings. All color references are to The Royal Horticultural Society Colour Chart except for colors having ordinary dictionary significance.

THE PLANT

Form: Tree.
Shape: Excurrent, pyramidal.
Height: 12.2 m (40').
Trunk Size: 37.08 cm (14.6").
Bark: Grayish-browh, furrowed into narrow somewhat rounded ridges.
Growth rate: Rapid, strength excellent.
Branches:
- *Angle of attachment.*—30°–60°, average 37°.
- *Spacing.*—Regular.
- *New branches less than* 0.5 *cm in diameter.*—Bark: reddish-brown. Lenticels: tan, elliptical, 2 mm long by 1 mm wide. Quantity: scattered, not prominent.
- *Branches greater than* 0.5 *cm in diameter.*—Bark: grayish-brown, prominent corky wings (to 1.5 cm) begin development on second year wood. Lenticels: inconspicuous.

Leaves:
- *Length.*—Petiole 10—13 cm, average 12.0; lamina 8–18 cm, average 13.1 cm.
- *Width.*—9–23 cm, average 16.2 cm.

*Form.*—Star-shaped, 5 lobed.

*Margin.*—Crenate-serrate.

*Texture.*—Leathery, glossy and glabrous.

*Pubescense distribution.*—Tan axillary tomentose in axis of principal veins.

*Quantity.*—Abundant, clustered beneath terminal bud.

*Color.*—Summer: Upper side: lustrous dark green, 137 A-B; lower side lighter than 137 A-B. Fall: When the tree is grown in the open, color ranges from deep burgundy to red; in a more confined or shaded area, fall color is usually yellow.

*Petioles.*—Length 10–13 cm, average 12.0 cm.

*Ribs and veins.*—5 primary veins.

*Thorns.*—None.

*Spines.*—None.

*Prickles.*—None.

Buds:

*Terminal on vegetative shoot.*—Imbricate, 6–8 scales, ovate to conical, reddish green-brown. Diameter:0.6–0.8 cm, Length: 1.3–1.7 cm.

*Terminal on spur.*—Imbricate, 6–8 scales, ovate to conical, reddish green-brown. Diameter: 0.4–0.7 cm, Length: 1.0–1.5 cm.

Fruit: Almost fruitless. Most of the fruit that develops aborts in mid-June when they are small and soft.

*Syncarp of dehiscent capsules.*—1.3–1.9 cm (0.5–0.75 in) diameter; persisting into winter; soft, not woody; sparse in comparison to the species, with very few remaining on the tree during winter.

It is claimed:

1. A new and distinct cultivar of sweet gum tree named 'Ward', as illustrated and described.

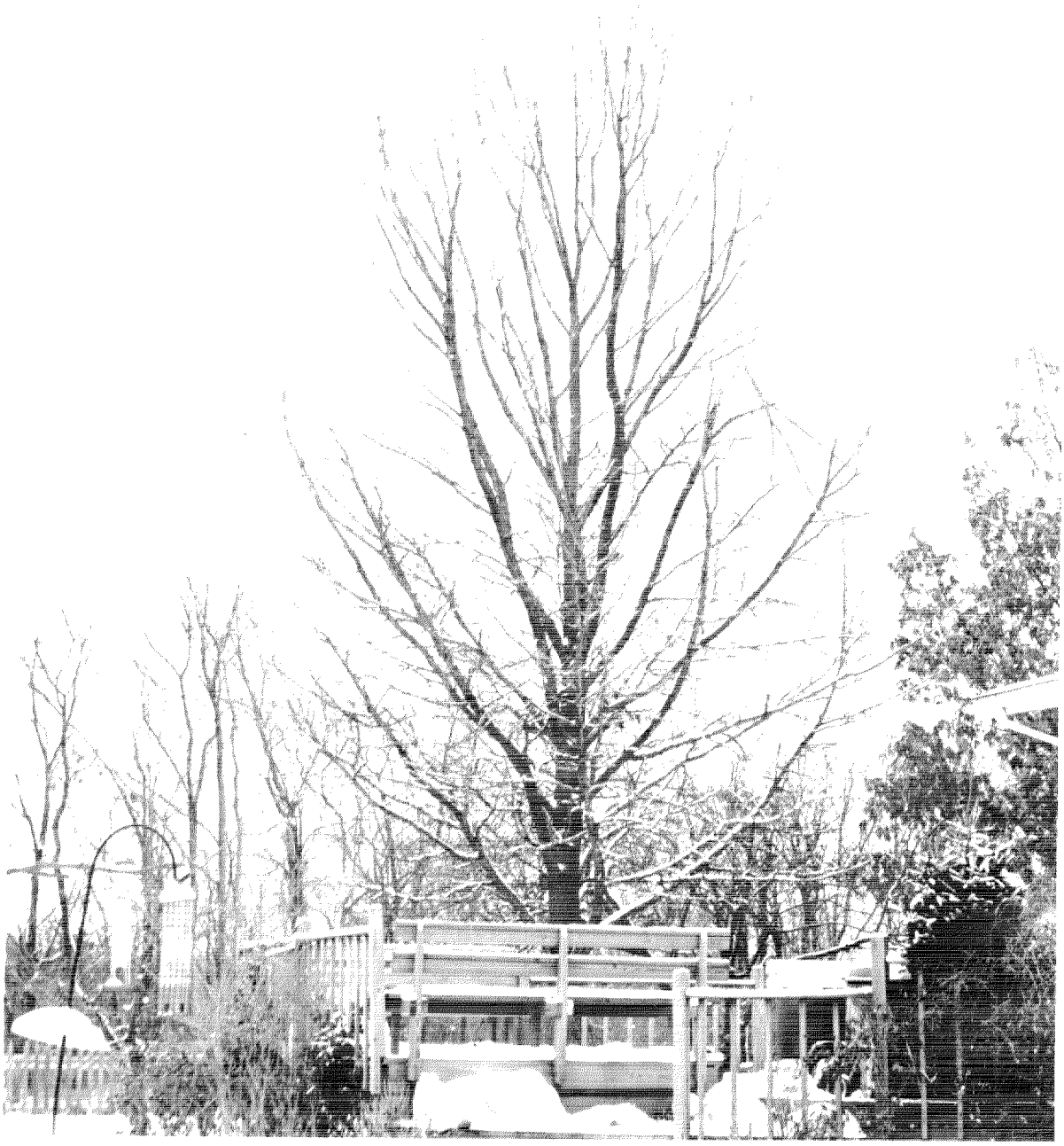

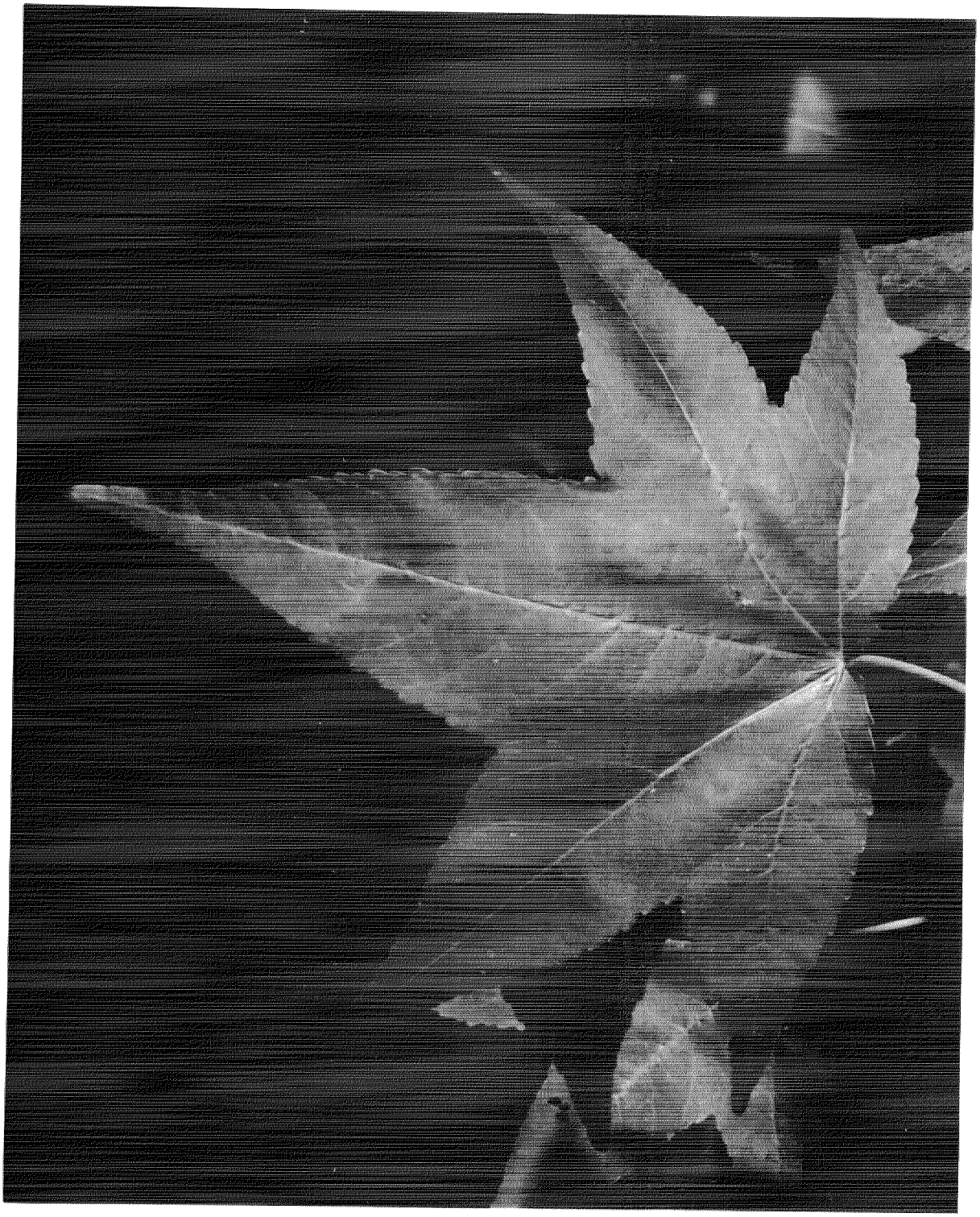

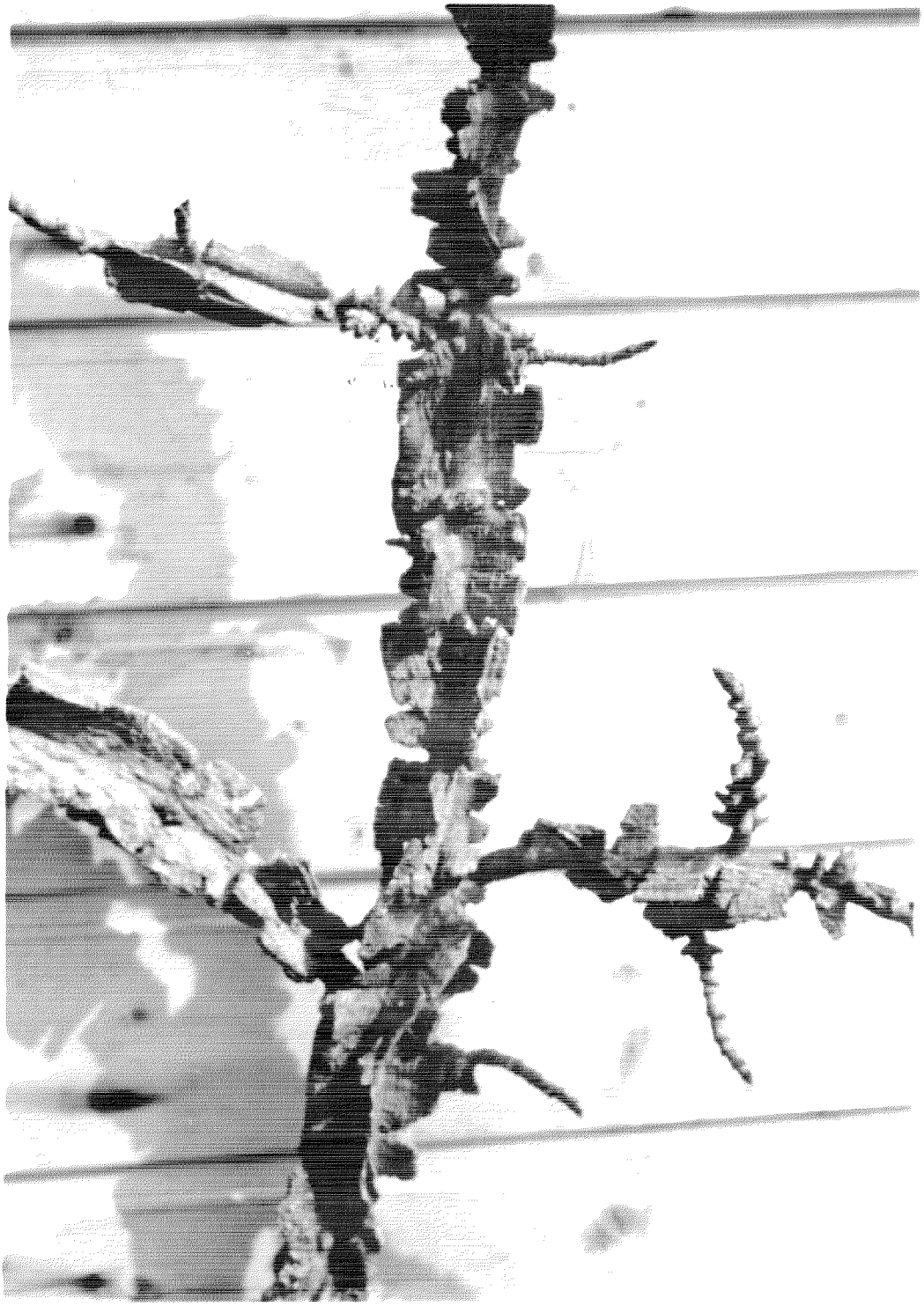

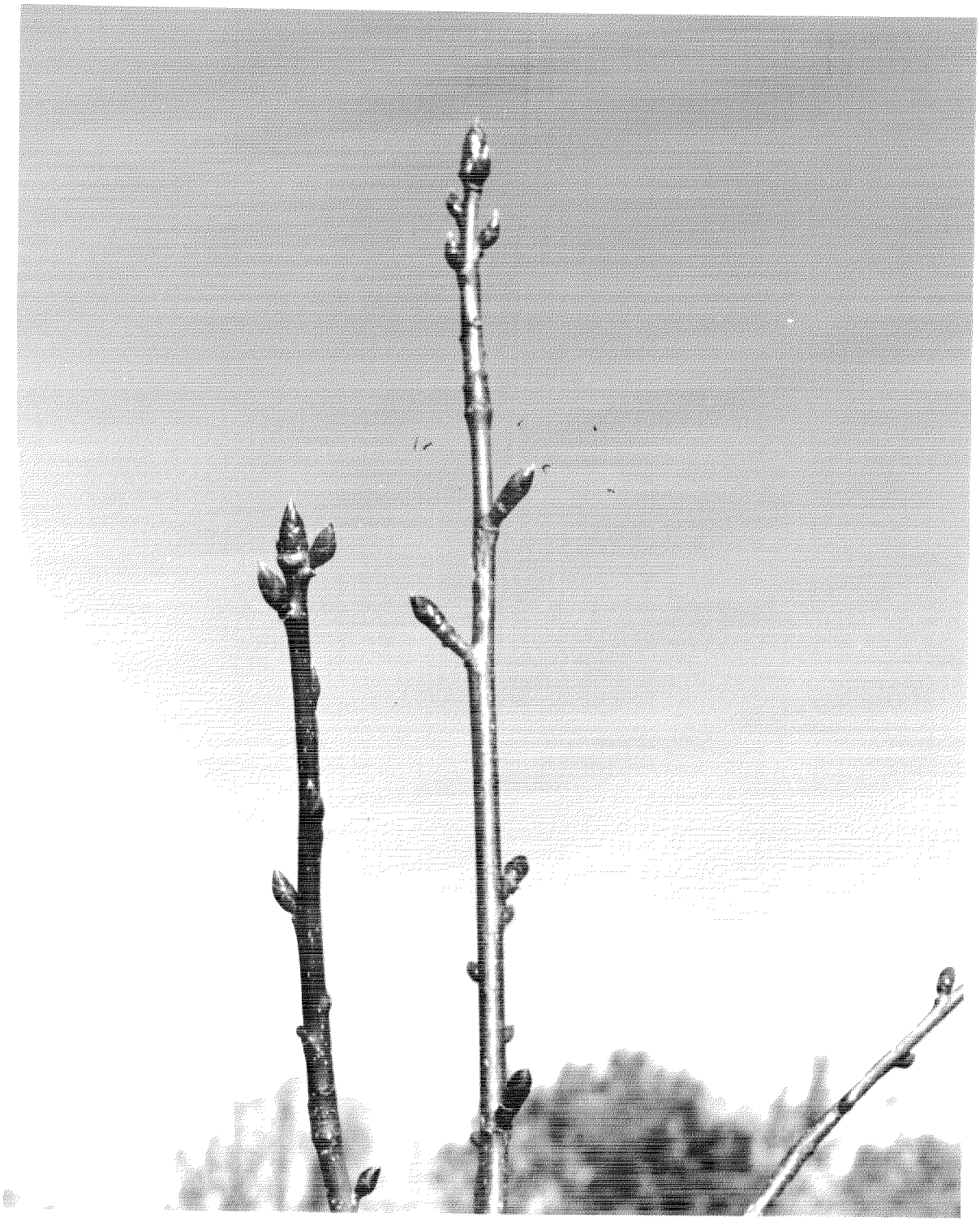

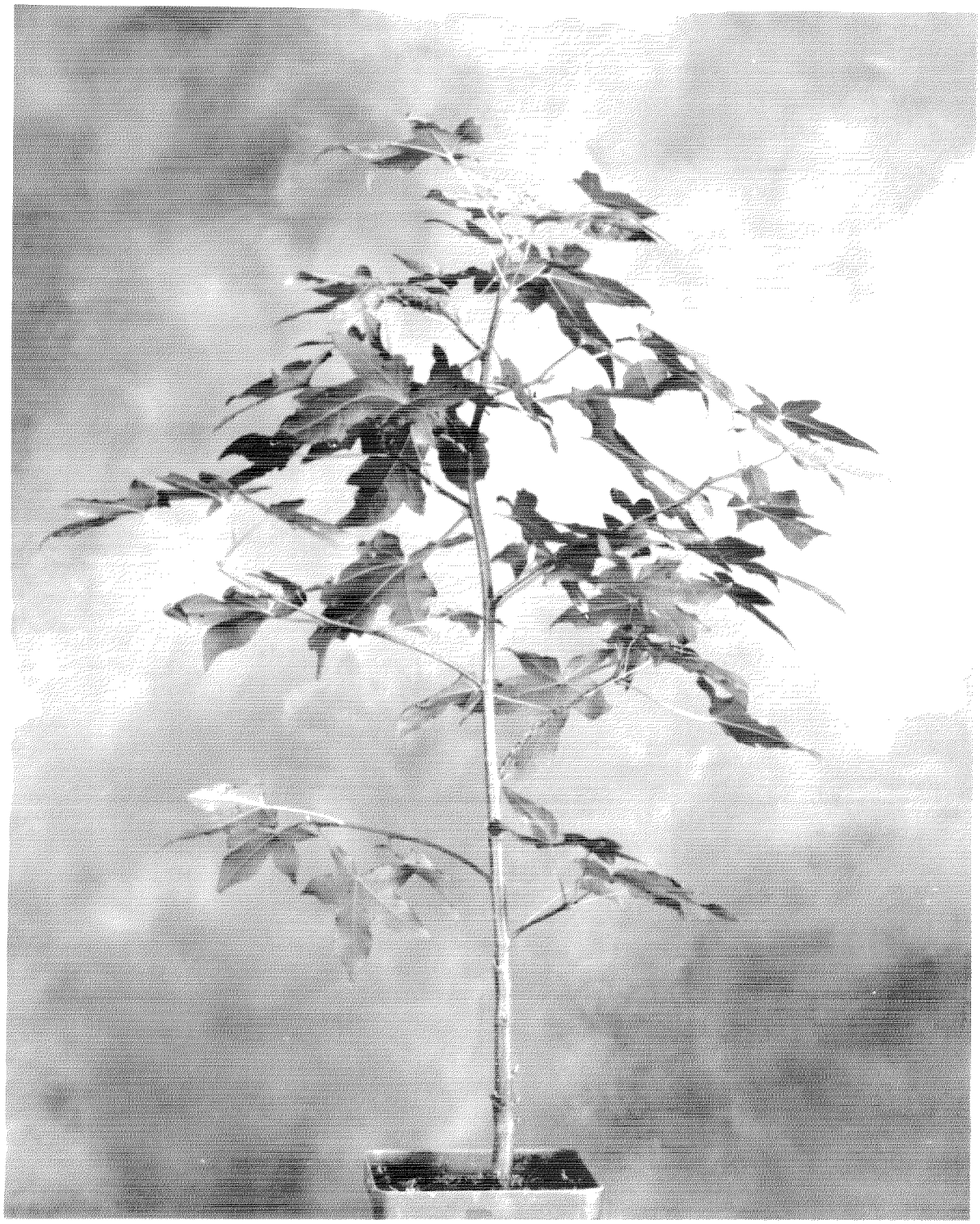

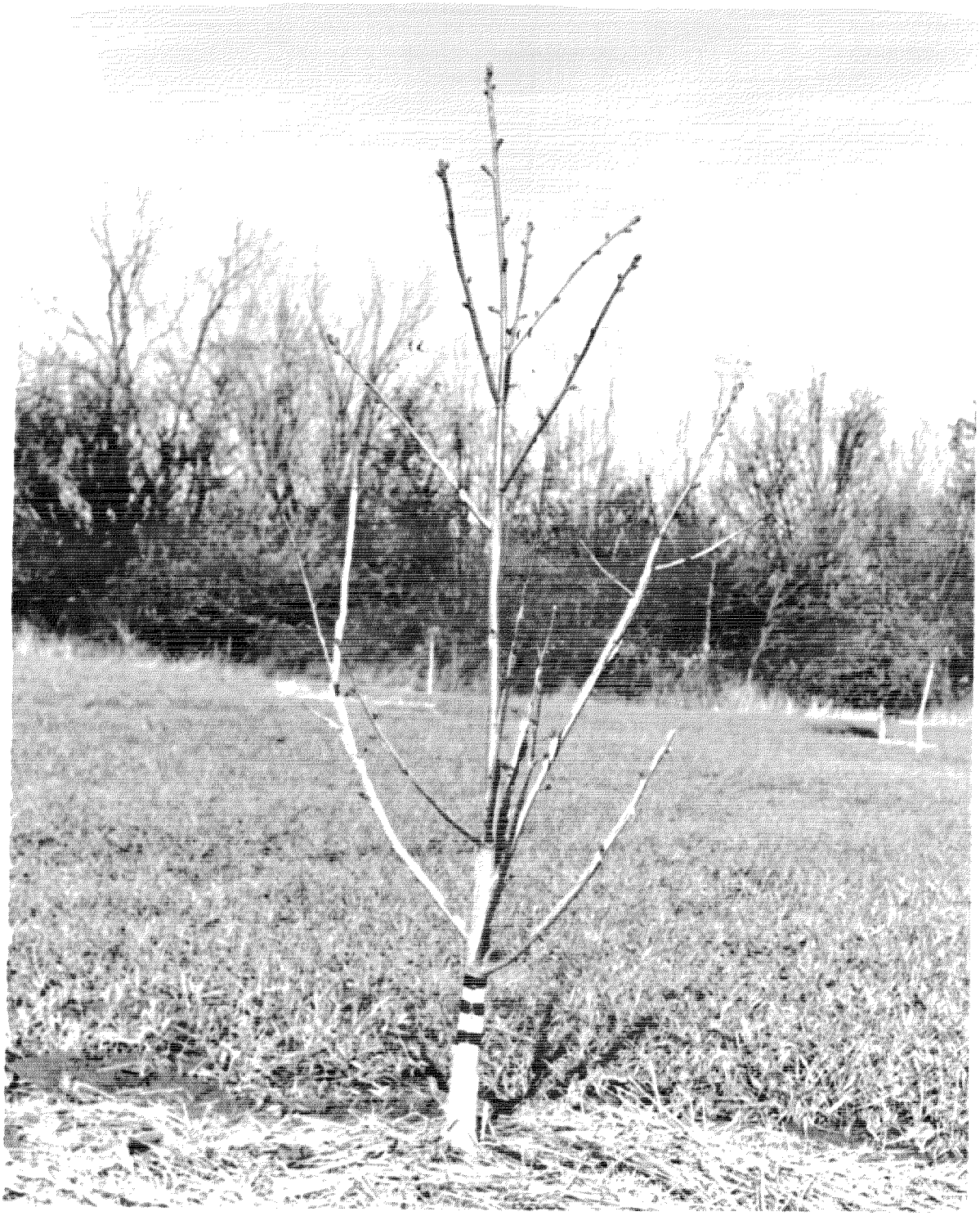

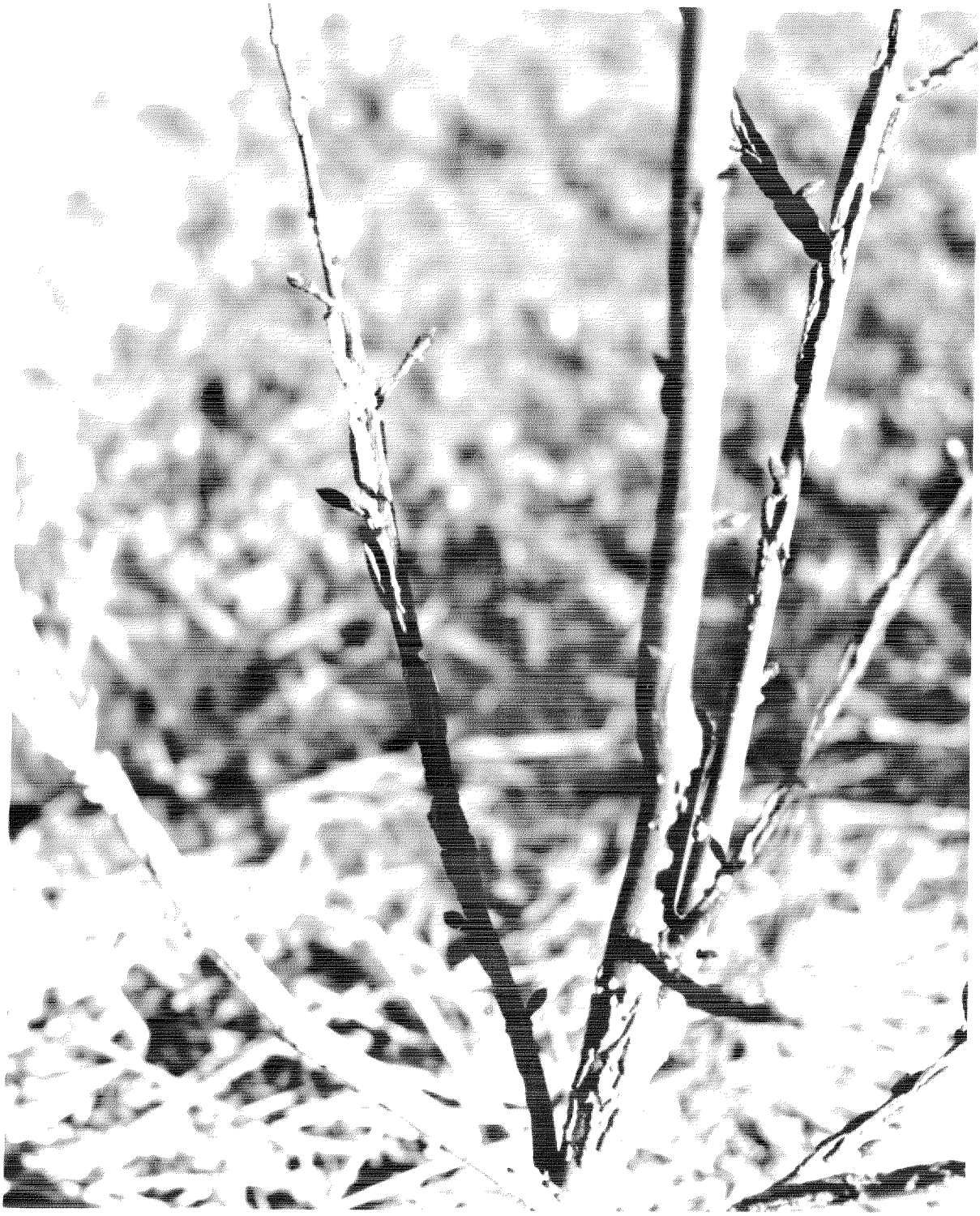

* * * * *